(12) United States Patent
Anders et al.

(10) Patent No.: US 6,368,587 B1
(45) Date of Patent: *Apr. 9, 2002

(54) BIOACTIVE SURFACE COATING USING MACROINITIATORS

(75) Inventors: Christine Anders, Haltern; Jochen Meier-Haack, Dresden; Volker Steinert, Dresden; Stefan Zschoche, Dresden; Robert Hans-Jörg Jacobasch, deceased, late of Dresden; by Margareta Ute Dagmar Jacobasch, Dresden; by Kathrin Götz, Berlin; by Lutz Jacobasch, Dresden; by Susanne Jacobasch, Berlin, all of (DE)

(73) Assignee: Huels Aktiengesellschaft, Marl (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/105,206

(22) Filed: Jun. 26, 1998

(30) Foreign Application Priority Data

Jun. 28, 1997 (DE) .......................... 197 27 555
Mar. 4, 1998 (DE) .......................... 198 09 042

(51) Int. Cl.[7] .................... A61K 31/74; A61L 27/16
(52) U.S. Cl. ..................... 424/78.18; 427/508; 427/340
(58) Field of Search ............... 424/78.18; 427/333, 427/337, 340, 379, 385.5, 388.1, 389.7, 393.5, 402, 407.1, 407.2, 409, 487, 497, 508, 520, 532, 553, 558; 523/122; 522/904

(56) References Cited

U.S. PATENT DOCUMENTS 4,256,782 A * 3/1981 Tazuke et al.
6,001,894 A * 12/1999 Ottersbach et al.
6,096,369 A * 8/2000 Anders et al.

FOREIGN PATENT DOCUMENTS

| DE | 2 242 818 | 3/1973 |
| DE | 3044531 C2 | 8/1981 |
| DE | 4034901 A1 | 4/1992 |
| DE | 197 20 369.8 | 6/1996 |
| EP | 0 379 477 A1 | 5/1990 |
| EP | 0 431 213 A1 | 6/1991 |
| WO | WO 92/18098 | 10/1992 |
| WO | WO 94/16648 | 8/1994 |

OTHER PUBLICATIONS

"A novel antimicrobial central venous catheter impregnated with benzalkonium chloride." S.E. Tebbs, et al., The British Society for Antimicrobial Chemotherapy, 1993, pp. 261–271.

"Staphylococcal Adherence to Modified Synthetic Polymer Surfaces." W. Kohnen, et al., Gustav Fischer Verlag, Stuttgart–Jena–New York, 1994, pp. 408–410.

"Macromolecular Prodrugs." T. Ouchi, et al. Progr. Polym. Sci., 1995, vol. 20, pp. 211–257.

* cited by examiner

Primary Examiner—Edward J. Webman
(74) Attorney, Agent, or Firm—Oblon, Spivak, McClelland, Maier & Neustadt, P.C.

(57) ABSTRACT

A process for the bioactive coating of the surface of substrates, which entails graft polymerizing at least one vinyl monomer of the formula (I):

$$R-(A)_a \qquad (I)$$

in which R is an olefinically unsaturated organic radical, having the valence a, A is a carboxyl group —COOH, sulfuric acid group —OSO$_2$OH, sulfonic acid group —SO$_3$H, phosphonic acid group —OPO(OH)$_2$, phosphoric acid group —PO(OH)$_2$, phosphorous acid group —OP(OH)$_2$, phenolic hydroxyl group or a salt of one of these groups, and a is an integer of from 1 up to and including 6, under radiative induction or thermally on a substrate surface which his been treated beforehand with a macroinitiator having groups which form free radicals in side chains of the polymer framework; with the proviso that a vinyl monomer I in which A is the carboxyl group —COOH or a salt of the carboxyl group contains at least one further radical A having a different one of the definitions specified for A or is used together with at least one further monomer I in which A has a different one of the definitions specified for A. If desired, a crosslinker may also be used for the coating. The present invention also provides articles whose surface is coated in whole or in part by the above process as well as various methods of use in the medical, biotechnological or hygiene fields.

25 Claims, No Drawings

BIOACTIVE SURFACE COATING USING MACROINITIATORS

BACKGROUND OF THE INVENTION

1. Field of the Invention

The present invention relates to a process for the bioactive coating of the surface of substrates, preferably plastic (or polymer) substrates using a macroinitiator. An important property of the coatings applied in accordance with the present invention is their high compatibility in contact with body fluids and tissue, especially with blood. Depending on the functionality of the coating monomers and on the molar ratio of certain functional groups in the coating, the surfaces, moreover, repel bacteria and inhibit cell proliferation, or repel bacteria and promote cell proliferation. The present invention additionally relates to products having surfaces coated in this way for use for medical or biotechnical purposes or in the hygiene sector.

2. Description of the Background

The colonization and multiplication of bacteria on surfaces is a phenomenon which is generally undesirable and is frequently associated with adverse consequences. For instance, in the drinking water and beverage industry bacterial populations may lead to a reduction in product quality and endanger health. Bacteria on or in packaging frequently bring about the decay of foods or even cause consumer infections. In biotechnical plaints that operate under sterile conditions, bacteria may be introduced with raw materials or may remain in all parts of the plant if sterilization is inadequate. By adhesion, sections of the bacterial population may escape the normal liquid exchange entailed in rising and cleaning and multiply within the system.

Bacterial colonies are also known in water treatment plants (for example, for membrane desalination) as well as in containers which have been filled with dissolved or liquid, undiluted organic substances offering advantageous conditions for bacterial populations. Such microbial colonization can, to a considerable extent, lead to the blocking and/or corrosive destruction of the plant.

Particular importance is attached to protecting against bacterial adhesion and propagation in nutrition, in human care, especially in the care of the elderly, and in medicine. In the case of large-scale outlets serving food or drinks, there are considerable risks especially when, rather than using disposable tableware with the attendant problem of wastage, reusable tableware is employed that is inadequately cleaned. Also known is the harmful propagation of bacteria in hoses and pipes which conduct foods, as well as their multiplication in storage containers and in textiles in a hot and damp environment, for example, in swimming baths. Facilities of this kind are preferred habitats for bacteria, as are certain surfaces in areas through which many people pass, for example in public transport vehicles, hospitals, telephone boxes and schools and especially in public toilets.

In the care of the sick and elderly, the often reduced defenses of those affected necessitate careful measures to counter infections, especially on intensive care wards and in the case of care at home.

Particular care is required in the use of medical articles and instruments in the case of medical investigations, treatments and interventions, especially when such instruments or articles come into contact with living tissue or with body fluids. In the case of long-term or permanent contact, especially in the case of implants, catheters, stents, cardiac valves and pacemakers, bacterial contamination can become a life-threatening risk to the patient. Diverse attempts have already been made to suppress the colonization and propagation of bacteria on surfaces. In J. Microbiol. Chemoth. 31 (1993), 261–271 S. E. Tebbs and T. S. J. Elliott describe paintlike coatings with quaternary ammonium salts as antimicrobial components. It is known that these salts are dissolved out of the coating material by water, by aqueous or by other polar media and by body fluids, and that their action is therefore short-lived. This applies equally to the incorporation of silver salts in coatings, as described in WO 92/18098.

T. Ouchi and Y. Ohya in. Progr. Polym. Sci. 20 (1995) 211 ff. describe the immobilization of bactericidal active substances on polymer surfaces by means of covalent bonding or ionic interaction. In such cases, the microbicidal actions are frequently reduced markedly relative to the pure active substance. Heteropolar bonds often prove to be of insufficient stability. Furthermore, the killing of the microbes leads in general to unwanted deposits on the surfaces, which mask the subsequent bactericidal action and form the basis for later bacterial colonization.

W. Kohnen et al. in ZBI. batch. sup. 26, Gustav Fischer Verlag, Stuttgart-Jena-New York, 1994, pages 408 to 41 0 report that the adhesion of *Staphylococcus epidermidis* on a polyurethane film is reduced if the film is pretreated by glow discharge in the presence of oxygen and is then grafted with acrylic acid.

The literature also describes the grafting of monomers onto substrates to which a peroxide-containing polymer has been applied beforehand as macroinitiator. In these systems, the photolytically or thermally cleavable groups are located in the polymer framework (DE 30 44 531, EP 0 370 477). In cleaving these groups to form free radicals, the polymer framework of the macroinitiator is broken down and thus loses its stability. Such a polymer cannot be applied to other substrates to form a permanent interpenetrating network (IPN), since the cleavage of the abovementioned groups forms small polymer fragments which diffuse out of the substrate network.

DE-A 22 42 818 describes the preparation of polymers containing peroxydiester groups in side chains, but does not indicate any specific use therefor.

As noted, it is important, when medical articles and instruments are used in medical investigations, treatments and interventions, that bacterial contamination of these articles and instruments is prevented. In the case of some of these articles and instruments, which come into medium- or long-term contact with living tissue or body fluids, moreover, the adhesion and propagation of endogenous cells is extremely undesirable. Thus cell colonization in the case of catheters applied intra-corporeally in the medium term is just as harmful as in the case of cardiac valves or stents which are implanted in the long term.

Furthermore, the transparency of intraocular lenses may experience a continuous decrease as a result of cell colonization after implantation. There is a range of processes aimed at avoiding cell colonization, for example by incorporating certain metals or metal salts into the mount of the intraocular lens, although the effect is usually incomplete and not durable. WO 94/16648, too, describes a process which is intended to prevent the proliferation of cells on the surface of implanted ocular lenses made from polymer material.

According to EP 0 431 213, polymers are to be furnished with cell-repelling properties by rendering their surface hydrophilic using strong mineral acids. The subsequent chemical modification of polymer surfaces, however, is in most cases not uniform. In general, there remain sites which have been treated not at all or not sufficiently and which constitute starting points for cell colonization. In addition, the cell-repelling properties of the surfaces treated in this way are in many cases not durable.

On the other hand, certain utilities require articles having surfaces which are repellent to bacteria but which promote cell colonization. This applies, for example, to a range of instruments for medical investigations, treatments and interventions, and also to some prostheses which are intended to grow into the tissue into which they have been implanted. Such instruments and prostheses, for example artificial hip joints or teeth, consist frequently of polymers or of other materials with a polymer coating, such as metals.

Finally, materials for instruments and devices which come into contact with body fluids, such as blood or lymph, or with tissue, must be compatible with their foreign environment. Blood compatibility in particular is an important desired property. The materials must therefore as far as possible have long blood coagulation times, i.e., minimal thrombogenic properties.

There are, therefore, various, in part mutually exclusive, requirements placed on the bioactive properties of the surface of polymers which are intended for medical uses. They are required always to be antibacterial and compatible with body fluids and tissue but should have an alternatively cell proliferation-inhibiting or -promoting action.

Thus, a need exists for bioactive materials or materials with bioactive surfaces thereon which are antibacterial and compatible with body fluids and tissues, but which also may have cell proliferation inhibiting or promoting action.

SUMMARY OF THE INVENTION

Accordingly, it is an object of the present invention to provide a process for the bioactive coating of the surface of substrates.

It is also an object of the present invention to provide an article having at least a portion of the surface thereof coated by the above process.

The above objects and others are provided by a process for the bioactive coating of the surface of substrates, which entails graft polymerizing at least one vinyl monomer of the formula (I):

in which R is an olefinically unsaturated organic radical, having the valence a, A is a carboxyl group —COOH, sulfuric acid group —OSO$_2$OH, sulfonic acid group —SO$_3$H, phosphonic acid group —OPO(OH)$_2$, phosphoric acid group —PO(OH)$_2$, phosphorous acid group —OP(OH)$_2$, phenolic hydroxyl group, or a salt thereof and a is an integer of from 1 up to and including 6, under radiative induction or thermally or a substrate surface which has been treated beforehand with a macroinitiator having groups which form free radicals inside chains of the polymer framework; with the proviso that a vinyl monomer I in which A is the carboxyl group —COOH or a salt of the carboxyl group, i.e. a carboxylate group, either contains at least one further radical A having a different one of the definitions specified for A or is used together with at least one further vinyl monomer I in which A has a different one of the definitions specified for A.

DETAILED DESCRIPTION OF THE PREFERRED EMBODIMENTS

In accordance with the present invention; it has surprisingly been discovered that the surface of substrates, especially of polymer substrates, can be given an advantageous bioactive coating, if at least one vinyl monomer of the formula (I):

in which R is an olefinically unsaturated organic radical, advantageously a hydrocarbon radical, having the valence a, A is a carboxyl group —COOH, sulfuric acid group —OSO$_2$OH, sulfonic acid group —SO$_3$H, phosphonic acid group —OPO(OH)$_2$, phosphoric acid group —PO(OH)$_2$, phosphorous acid group —OP(OH)$_2$, phenolic hydroxyl group, or a salt thereof, i.e., of any one of these groups, and a is an integer of from 1 up to and including 6, preferably 1, 2 or 3, is subjected to a graft polymerization under radiative induction or thermally on a substrate surface which has been treated beforehand with a macroinitiator having groups which form free radicals in side chains of the polymer framework; with the proviso that a vinyl monomer I in which A is the carboxyl group —COOH or a salt of the carboxyl group (in other words a carboxylate group), either contains at least one further radical A having a different definition as specified for A or is used together with at least one further vinyl monomer I in which A has a different definition as specified for A.

In an advantageous embodiment of the present invention, use is made not only of a monoolefinically unsaturated vinyl monomer I, but instead also of a crosslinking vinyl monomer which has at least 2, and if desired 3 or 4 olefinic double bonds. The crosslinking vinyl monomer can itself contain groups A, and in that case is therefore a vinyl monomer I and is itself bioactive. In this case, a monolefinically unsaturated vinyl monomer I can, but does not have to be, used in addition. If, however, the crosslinking vinyl monomer is free of group A, a monoolefinically unsaturated vinyl monomer I must be used in addition. The crosslinker can be applied to the substrate which was already treated with the macroinitiator, if desired together with a monoolefinically unsaturated vinyl monomer I. However, it is advantageous to add the crosslinker to the solution of the macroinitiator, if the substrate is being treated with the latter.

The common feature of the monomers of the formula I is that they have 1 or 2 olefinic double bonds and also at least one acidic group or a salt of an acidic group. Among the salts, the alkali metal salts, and especially the sodium salts, are preferred. Acidic groups, such as carboxylic and sulfonic acid groups, can be converted by neutralization (for example with sodium hydroxide or in phosphate buffers), after grafting, into carboxylate and sulfonate groups, respectively, and carboxylate groups can be acidified to give carboxyl groups. In the latter cases, therefore, one particular group A is transformed into another group A.

Surprisingly, the antibacterial properties of the surfaces coated in accordance with the invention with a carboxyl- or carboxylate-functional monomer I together with another monomer I are markedly more pronounced than is the case with the modification of acrylic acid according to W. Kohnen et al., loc. cit., under comparable conditions.

The surfaces coated in accordance with the invention display a remarkable combination of advantageous properties and are therefore of outstanding physiological compatibility. They are, in particular, highly compatible with blood and reduce the adhesion and propagation of bacteria to a high extent even over quite a long period. Bacteria affected by this action include *Staphylococcus aureus, Staphylococ-* cus epidermidis, Streptococcus pyogenes, Klebsiella pneumoniae, Pseudomonas aeruginosa and Escherichia coli. At the same time there is also inhibition in most cases of the proliferation of cells, for example of fibroblasts and endothelial cells, such as human umbilical cord cells. The particular conditions under which a coating has an antibacterial but cell proliferation-promoting action are explained below. The surfaces of the substrates coated in accordance with the invention are free from migratable and/or extractable monomer and oligomer components. Unwanted side effects resulting from released exogenous substances or from dead bacteria are avoided from the outset.

The co-use of a crosslinker results in coatings which adhere better and are more stable to delamination. This is particularly true if the crosslinker is used together with the macroinitiator in treating the substrate.

In the process according to the invention the substrate surfaces are first of all treated, as described in more detail below, with a macroinitiator having groups which form free radicals, in the side chain, and then are coated under the action of UV light or heat by nonaggressive graft polymerization or graft copolymerization.

The Vinyl Monomers of the Formula (1)

The graft (co)polymerization is advantageously conducted with polymerizable vinyl monomers, or mixtures of vinyl monomers, of the formulae (II) or (III):

In the formulae which are included in the formula 1, n independently at each occurrence is an integer from 2 up to and including 6, x independently at each occurrence is 1 or 2;

q independently at each occurrence is 0 or, if n=4, 5 or 6, is 2; and the radical $R^1$ independently at each occurrence is —H or one equivalent of a metal ion, especially an alkali metal ion.

In accordance with the definitions given the radical $(C_nH_{2n-q-x})$-independently at each occurrence is a straight-chain or branched monovalent alkenyl radical (q=0, x=1) or alkadienyl radical (q=2, x=1) or a divalent alkenylene radical (q=0, x=2) or alkadienylene radical (q=2, x=2).

Instead of two vinyl monomers II and III it is also possible to employ only one monomer (II+III, which contains the groups —$COOR^1$ and —$SO_3R^1$ in the same molecule.

In addition, benzene-derived monomers of the formula (IV):

can be employed in which

B independently at each occurrence is a mono- or divalent straight chain or branched radical of the formula $(C_nH_{2n-l-q-y})(COOR^1)_y$ or $(C_nH_{2n-l-q-x})(SO_3R^1)_y$, where $R^1$, n and q are as defined above; and y is 0, 1 or 2;

$R^3$ independently at each occurrence is $C_{1-4}$-alkyl, —$NH_2$, —COOH, —$SO_3H$, —$OSO_3H$, —$OPO(OH)_2$, —$PO(OH)_2$, —$OP(OH)_2$, —$OPO(O^-)OCH_2$—$CH_2$—$N^+(CH_3)_3$, —$PO(O^-)O$—$CH_2$—$CH_2$—$N^+(CH_3)_3$, —$OP(O^-)PCH_2$—$CH_3$—$N^+(CH_3)_3$ or a salt, especially an alkali metal salt, of said acidic groups;

y is 0, 1 or 2;

b is 1, 2 or 3;

c is 0, 1, 2, or 3; and d is 0, 1, 2 or 3;

with the proviso that b+c+d≦6, advantageously ≦4.

It is, of course, also possible to employ any desired mixture of vinyl monomer of the formulae II, III and IV for the process according to the present invention.

Other suitable vinyl monomers are, corresponding to the formula I, sulfuric acids and their salts, sulfonic acids and their salts, phosphonic acids and their acidic or neutral salts, acidic phosphonic esters and their salts; phosphoric acids and their acidic or neutral salts, acidic phosphoric esters and their salts- and phosphorous acids and their acidic or neutral salts, their acidic esters and the salts thereof. These monomers as well can be used in a mixture with one another and/or with the monomers of the formulae II, III and IV for the process according to the invention.

Finally, mention may also be made of phenols having a valence (or basicity) of from 1 to 3, and also their salts, corresponding to the formula 1, as suitable monomers. These too are optionally employed as a mixture with one another and/or with the abovementioned vinyl monomers.

For the process according to the present invention it has proven worthwhile to use a combination of vinyl monomers I which leads to coatings which on the one hand have carboxyl and/or carboxylate groups and on the other hand have sulfonic acid and/or sulfonate groups. From the standpoint of compatibility with regard to said groups there are three possible two-way combinations, namely carboxyl-sulfonic acid groups, carboxyl and sulfonate groups, and carboxylate and sulfonate groups, and also two three-way combinations, namely carboxyl, carboxylate and sulfonate groups, and carboxyl, sulfo acid and sulfonate groups. All of these combinations constitute useful embodiments of the process according to the present invention.

In the abovementioned combination the molar ratio of carboxyl and/or carboxylate groups to sulfonic acid and/or sulfonate groups in the coating can fluctuate within wide limits. Particularly pronounced cell proliferation inhibiting properties are obtained if said ratio is from about 0.2 to 3, advantageously from about 0.4 to 3, and, in particular, from about 0.4 to 2. The coated surfaces exhibit, in a remarkable manner, antibacterial but cell proliferation-promoting properties if said molar ratio is from about 2 to 10, advantageously from about 3 to 10 and, in particular, from about 3 to 5. A coating is cell proliferation-promoting for the purposes of the invention when the adhesion and multiplication of mammalian cells is improved by the coating, in comparison with the uncoated surface, or at least is less severely impaired than the adhesion and multiplication of bacteria.

Of the suitable monomers of the formula I which contain one or more identical or different radicals A in the molecule, mention may be made, by way of example, of: acrylic acid, sodium acrylate, 4-vinylsalicylic acid, itaconic acid, vinylacetic acid, cinnamic acid, 4-vinylbenzoic acid, 2-vinylbenzoic acid, sorbic acid, caffeic acid, maleic acid, methylmaleic acid, crotonic acid, isocrotonic acid, fumaric acid, methylfumaric acid, dimethylfumaric acid, dihydroxymaleic acid, allylacetic acid-I allylsulfuric acid, allylsulfonic acid, methallylsulfuric acid, methallylsulfonic acid, sodium allyl sulfate, sodium allylsulfonate, sodium methallyl sulfate, sodium methallylsulfonate, sodium vinylsulfonate, vinyl-sulfonic acid, 4-vinylbenzenesulfonic acid, 2- or 4-styrenesulfonic acid, sodium 2- or 4-styrenesulfonate, sodium vinyltoluenesulfonate; 2-butene-1,4-diol diphosphate, 2-butene-1,4-diol diphosphonate, the disodium salts of the diphosphate and diphosphonate, respectively, 2-vinylphenol, 2-allylhydroquinone, 4-vinylresorcinol, m-hydroxystyrene, o-hydroxystyrene, p-hydroxystyrene and carboxyl-vinylbenzenesulfonic acid.

In a further embodiment of the process according to the invention use is made as monomer I of a mixture of monomers of formula (V) and (VI):

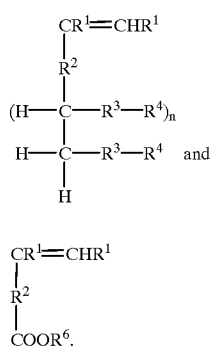

In the formulae I and II:

R$^1$ is hydrogen or a methyl radical,

R$^2$ is a divalent organic radical, preferably an aliphatic, cycloaliphatic or aromatic hydrocarbon radical having up to 1 0 carbon atoms, or a C—C single bond, R$^3$ is —O— or —NH—, R$^4$ is hydrogen or the radical —SO$_3^-$Na$^+$, R$^5$ is hydrogen, the methyl radical or the radical —R$^2$—COO$^-$Na$^+$, R$^6$ is hydrogen or Na, and n is 4 or 5;

with the proviso that at least one of the substituents R$^4$ is a radical —SO$_3^-$Na$^+$.

In preferred monomers V and VI:

R$^1$ is hydrogen or a methyl radical,

R$^2$ is an alkylene radical having 1 to 4 carbon atoms, a phenylene radical or a C—C single bond, R$^3$ is —O— or —NH—, R$^4$ is hydrogen or the radical —SO$_3^-$Na$^+$, R$^5$ is hydrogen or the radical —R$_2$—COO$^-$Na$^+$, R$^6$ is hydrogen or Na and n is 4.

The monomers V include modified sugar residues, preferably from pentoses and, in particular, from arabinose. The sugar residues comprise at least one of the radicals —O—SO$_3^-$Na$^+$ (O-sulfate) or —NH—SO$_3^-$Na$^+$ (N-sulfate), preferably, adjacent to the radical R$^2$. They have preferably 1 to 4 of these radicals. O-sulfate and N-sulfate radicals can be present simultaneously in one sugar residue, in which case the N-sulfate radical is preferably positioned adjacent to the radical R$^2$. Alternatively, however, the sugar residue may comprise exclusively one kind of these radicals, for example only O-sulfate radicals. Each of the species specified (residues containing only O-sulfate and residues containing N-sulfate) is suitable, alone or together with the other species, as monomer V. The mixing proportion is therefore from 0:100 to 100:0.

The quantitative proportions in which the monomers V and VI are employed can fluctuate within wide limits. Thus the molar ratio of the N-sulfate and/or O-sulfate groups of the monomer V to the carboxyl and/or carboxylate groups of the monomer VI can be, for example, from about 1:100 to 100:1. Preferred molar ratios are between about 1:20 and 20:1.

The preparation of the monomers V is described in detail in German Patent Application 197 20 369.8 (O.Z. 5195).

Monomers VI are known and readily obtainable substances which contribute the carboxyl or carboxylate groups that are required for the heparin-analogous action. Suitable monomers VI have one olefinic double bond and one or two carboxyl and/or carboxylate functions, or functions which can be transformed into carboxyl and/or carboxylate functions, such as carboxylic ester groups, carboxamide groups or carboxylic anhydride groups. Sodium ions are used as counterions to the carboxylate function. Examples of suitable monomers VI are (meth)acrylic acid, crotonic acid, 4-vinylbenzoic acid, maleic acid, fumaric acid, itaconic acid, vinylacetic acid, cinnamic acid, isocrotonic acid, methylmaleic acid, dimethylfumaric acid, methylfumaric acid, dihydroxymaleic acid, allylacetic acid and their sodium salts.

Other Vinyl Monomers

It is of course also possible to employ other vinyl monomers instead of or in addition to vinyl monomers I, the functional groups of these other vinyl monomers being changed after the graft polymerization. For example, carboxamide groups can be transformed subsequently, by hydrolysis in an acidic medium, into carboxyl groups. Furthermore, carboxylic ester groups and sulfonic ester groups can be converted into carboxylate and sulfonate groups, respectively, by hydrolysis in an alkaline medium. Examples of other vinyl monomers having functional groups which can be transformed into groups A are the esters, amides and nitriles of the acids listed by way of example under 4.1, especially with alkanols having 1 to 8 carbon atoms, and also acrylonitrile and methacrylonitrile.

It is possible in addition to use, as well, vinyl monomers which contain no groups A and no groups which can be transformed into groups A, and which are therefore neutral or have at best a weak effect in terms of the biological action. Examples of these include vinyl esters such as vinyl acetate and vinyl propionate-vinyl ketones, such as vinyl ethyl ketone; olefins, such as 1-butene, 1-hexene and 1-octene; vinylaromatic compounds, such as styrene, vinyltoluene and divinylbenzene; and vinylsiloxanes.

The other monomers can even be present in a predominant amount, for example accounting for up to 90 mol %.

Crosslinking Vinyl Monomers

The crosslinking vinyl monomers have at least 2, if desired 3 or 4 olefinic double bonds. Using them leads firstly to thicker coats which are more stable to delamination, and secondly to a further reduction in bacterial adhesion and multiplication under otherwise identical conditions. Crosslinkers having 3 or 4 olefinic groups are to this extent markedly more effective than diolefins. These lead to two-dimensional networks, while the preferred vinyl monomers of higher functionality give three-dimensional networks. It is of course also possible to work with two or more different crosslinkers.

As already mentioned, the crosslinking vinyl monomer can itself include groups A; it is then a vinyl monomer I and contributes to the bioactivity of the coating. Alternatively, it may comprise a functionality which can be transformed into groups A, or may be free from functional groups. The use of crosslinkers with 3 or 4 olefinic double bonds is particularly advisable when a vinyl monomer I having two olefinic double bonds is employed for grafting.

The crosslinking vinyl monomers judiciously contain hydrophilic groups, for example hydroxyl and/or alkylene oxide groups, and are then simultaneously hydrophilic and crosslinking vinyl monomers. If the crosslinker is added to the solution of the macroinitiator for treating the substrate, it is judiciously employed in amounts from 0.01 to 300 mole percent, advantageously from 10 to 150 mole percent, based on the peroxide groups of the macroinitiator. If the crosslinker is used together with the monoolefinically unsaturated vinyl monomers I, it is judiciously employed in amounts of 0.1 to 50 mole percent, advantageously from 1 to 20 mole percent, based on the monoolefinically unsaturated vinyl monomers I.

Examples of suitable crosslinking vinyl monomers are lower diolefins, such as 1,3-butadiene and isoprene; (meth) acrylic acid derivatives, such as methylenebisacrylamide (MBAA), ethylene glycol dimethacrylate (EGDMA), diethylene glycol dimethacrylate, ethylene glycol diacrylate (EGDA), diethylene glycol diacrylate (DEGDA), tetraethylene glycol diacrylate or -methacrylate, polyethylene glycol 400 diacrylate, polyethylene glycol 600 diacrylate, polyethylene glycol 1000 diacrylate, trimethylol propane triacrylate, trimethylol propane trimethacrylate and pentaerythritol tetraacrylate; polyvinyl ethers, such as diethylene glycol divinyl ether, polyethylene glycol 300 divinyl ether, polyethylene glycol 1500 divinyl ether, polyethylene glycol 6000 divinyl ether, 1,4-cyclohexanedimethanol divinyl ether, 1,4-hexanediol divinyl ether, glycerol 12 EO trivinyl ether and pentaerythritol 64 EO tetravinyl ether-, carbohydrate derivatives, such as acryloylated hydroxypropylcellulose having more than one acryloyl group per molecule; and allyl compounds, such as allyl cinnamate, tetraethylene glycol diallyl ether and pentaerythritol triallyl ether.

Substrate Materials

Particularly suitable substrate materials are all polymeric plastics, such as polyurethanes, polyamides, polyesters and polyethers, polyether-block-amides, polystyrene, polyvinyl chloride, polycarbonates, polyorganosiloxanes, polyolefins, polysulfones, polyisoprene, polychloroprene, polytetrafluoroethylene (PTFE), corresponding copolymers and blends, and also naturally occurring and synthetic rubbers, with or without radiation-sensitive groups. The process according to the invention can also be applied to surfaces of painted or otherwise polymer-coated metal, glass or wooden structures. The polymeric substrates can have many different shapes. For example, they can be in the form of sheets, films, tubes or hoses, depending upon the intended use of the product in question.

The Macroinitiator

Suitable macroinitiators comprise, in side chains, photolytically or thermally activatable, free-radical-forming groups, for example peroxide, hydroperoxide, perester or azo groups. They are synthesized, for example, by polymer-analogous reaction of carboxyl-containing polymers with peroxy alcohols or with hydrogen peroxide and then with carbonyl chlorides. An alternative synthesis starts from hydroxyl-containing polymers, which are reacted with hydrazine and then oxidized to the azo compound. Particularly suitable polymers are those prepared from monomers which on the one hand contain functional groups which permit attachment to or conversion to a photolytically or thermally activatable, free-radical-forming group and which on the other hand are homo- or co-polymerizable by addition polymerization, polycondensation or polyaddition. Preferred polymers are the carbon-framed copolymers or polymers that are obtainable by polymerization or copolymerization. If comonomers are used as well, the copolymers can be block copolymers or copolymers with a random or alternating sequence of monomers.

Suitable polymerizable monomers include those having hydroxyl groups, such as hydroxyalkyl (meth)acrylates, examples being hydroxyethyl methacrylate, 3-hydroxypropyl acrylate, 3-hydroxypropyl methacrylate or -4-hydroxybutyl acrylate; 3-hydroxystyrene, 4-hydroxy styrene, 4-vinylresorcinol, allyl alcohol, 2,3-butadiene-1-ol, 2-butene-1,4-diol, 2-butene-1-ol and 3-methallyl alcohol. Also suitable are monomers having carboxyl groups, such as acrylic acid, methacrylic acid, maleic acid, di-hydroxymaleic acid, fumaric acid and 4-vinylbenzoic acid- having epoxy groups, such as glycidyl (meth)acrylate, having anhydride groups, such as maleic anhydride-, or having imide groups, such as maleimide.

Treatment of the Polymer Substrate with the Macroinitiator

The macroinitiator is first of all dissolved in an organic solvent, if desired together with a crosslinker. Examples of suitable solvents are alcohols such as methanol, ethanol, propanol and isopropanol, ethers such as diethyl ether, tetrahydrofuran and dioxane- esters, such as ethyl acetate- ketones, such as acetone, methyl ethyl ketone and cyclohexanone; hydrocarbons, such as pentane, hexane, cyclohexane, white spirit, benzene, toluene or xylene, carboxylic acids, such as formic acid and acetic acid; halogenated hydrocarbons, such as dichloromethane, trichloromethane and tetrachloromethane- or strongly polar solvents, such as dimethylformamide, dimethylacetamide and dimethyl sulfoxide. It is of course also possible to employ homogeneous mixtures of two or more of said solvents. The solvents should on the one hand evaporate as rapidly as possible following treatment of the substrate but should also swell the substrate partly in order to enable the macroinitiator to penetrate into the structure (or an "alloy" with the structure) of the substrate. A favorable solvent for a given combination of macroinitiator and polymeric substrate can be found without difficulty by means of guideline experiments.

The concentration of the macroinitiator in the solution is judiciously from 0.5 to 60% by weight, in particular from 1 to 10% by weight. The concentration of the crosslinker which is also used, if desired, generally lies in the same range. The latter concentrations have been found particularly suitable in practice and generally give rise in one pass to coherent layers of the macroinitiator, and if desired a crosslinker, which cover the substrate fully and have layer thicknesses in the nm range. The substrate is treated with the solution, for example by dipping, brushing or spraying, and then is dried, at room temperature or at slightly elevated temperature and with or without reduced pressure, depending on the solvent and on the thermal sensitivity of the macroinitiator.

Coating with Vinyl Monomers Thermal Grafting

The vinyl monomer or monomers is or are applied, if desired together with a crosslinker, judiciously in dissolved form and again, for example, by dipping, brushing or spraying, to the polymer substrate which has been treated with the macroinitiator. The monomer coated substrate is then, depending on macroinitiator, heated in the absence of atmospheric oxygen at from 30 to 120° C., in particular at from 50 to 90° to initiate graft polymerization. Alternatively, the substrate with the macroinitiator can also be dipped into the vinyl monomer or monomers or into its/their solution and can be heated to the abovementioned temperatures in the immersed state. Depending on the vinyl monomer, examples of suitable solvents are water or aqueous alcohol mixtures, although other solvents or solvent mixtures can also be used provided they have sufficient solvency for the vinyl monomer and if desired for the crosslinker. Depending on the solubility of the monomers and the desired layer thickness, the concentration of the vinyl monomers and if desired the crosslinkers in the solution can be together from 0.1 to 40% by weight, preferably from 1 to 10% by weight. The latter concentrations have proven particularly suitable and generally result in one pass in coherent coats which fully cover the macroinitiator.

Photoinitiated Grafting

As a variant to the thermal grafting of the vinyl monomers, photoinitiated grafting is also possible. For this purpose the vinyl monomers, if desired together with a crosslinker, are applied as described to the substrate that has been treated with the macroinitiator, and the coated substrates are then irradiated. As an alternative, the substrates can also be irradiated in the immersed state. The temperatures during irradiation are in both cases judiciously from 20 to 60° C.

Irradiation takes place judiciously with rays in the shortwave segment of the visible region or in the long-wave segment of the UV region of electromagnetic radiation. Highly suitable rays are those having wavelengths of from 260 to 500 nm, preferably from 290 to 320 nm. Rays in the abovementioned wavelength range are relatively soft and selective with regard to polymerization; in other words, they attack neither the substrate polymer nor the framework of the macroinitiator. Particularly suitable radiation sources are Excimer UV lamps (from Heraeus, D-63801 Kleinostheim) with continuous radiation, for example with XeCl or XeF as the radiation medium. In principle, mercury vapor lamps with a broad UV spectrum and with radiative components in the visible range or in the abovementioned range can also be used. The exposure times are in general from 10 seconds to 20 minutes, preferably from 1 to 15 minutes, at radiative intensities in the range from 30 to 200 mW/cm$^2$.

It is sometimes judicious to repeat the operations described above, including the treatment with the macroinitiator, in order, by means of such a multicoat technique, to ensure a hermetically sealed and/or a thicker coating.

Use of the Coated Substrates

The process according to the invention permits the precise establishment of molar ratios of different functional groups which are optimal for inhibiting bacterial adhesion and/or propagation and for the desired character of the surface in terms of cell proliferation, or lead to improved blood compatibility. Articles with a surface coated in accordance with the invention are suitable for use in the medical or biotechnical field or in the hygiene sector. Examples of such articles are films, hoses, pipelines, door handles and toilet seats. Examples from the medical sector that may be mentioned include catheters, 2 5 implants (such as cardiac valves and stents), blood bags, dressings, hoses (for example for drainage tubes), membranes and contact lenses.

The present invention will now be further described by reference to certain examples which are provided solely to illustrate the present invention and are not intended to be limitative. The vinyl monomers used therein are representative of a large number of other suitable compounds which fall under the general formulae I to VI.

EXAMPLES

Polymer Substrates Used

TABLE 1a

Films

| Film No. | Polymer | Name, source | Manufacturer |
| --- | --- | --- | --- |
| F1 | polyamide 12 | VESTAMID, HÜLS AG | extrusion |
| F2 | polystyrene | VESTYRON, HÜLS AG | compression molding |
| F3 | polyurethane | PELLETHANE 2363-A, DOW CHEMICAL COMPANY | extrusion |
| F4 | polyether-block-amide | VESTAMID, HÜLS AG | extrusion |
| F5 | polyethylene | VESTOLEN A, VESTOLEN GmbH | extrusion |
| F6 | polypropylene | VESTOLEN P, VESTOLEN GmbH | extrusion |
| F7 | polyorgano-siloxane | NG 37-52, SILICON GmbH; D-01612 Nünchritz | knife coating |
| 8F | PVC | VESTOLIT P + DEHP, VESTOLIT GmbH | Brabendering |
| F9 | PTFE | HOSTAFLON, HOECHST AG | extrusion |
| F10 | polyurethane | TECOFLEX, THERMEDIX | extrusion |

TABLE 1b

Hoses

| Hose No. | Polymer | Name, Source | Preparation |
| --- | --- | --- | --- |
| Hose 1 | Polyethylene | VESTOLEN A, VESTOLEN GmbH | Extrusion |
| Hose 2 | Polyether-block-amide | PEBAX 5533 ATOCHEM S.A. | Extrusion |
| Hose 3 | Polyamide | VESTAMID, HULS AG | Extrusion |
| Hose 4 | Polyurethane | TECOFLEX, THERMEDIX GmbH | Extrusion |
| Hose 5 | Polyethylene | PELLETHANE 2563-A, DOW CHEMICAL CO. | Extrusion |

The Macroinitiators Used

Polymers with peroxy ester groups are used as macroinitiators. They are employed as 5% strength by weight solutions in the solvents indicated in Table 2.

TABLE 2

Macrointiators

| Macro-initiator No. | Copolymer of | Perester content | Degree of polymerization | Solvent |
|---|---|---|---|---|
| M1 | propene-maleic acid[1] | 10.8% | 140 | isopropanol/acetone 30:1 |
| M2 | α-methylstyrene maleic acid | 15.1% | 270 | THF/acetone/—H₂O; 1:1:4 |
| M3 | ethene-maleic acid | 15.3% | 95 | isopropanol/H₂O/THF 5:5:1 |
| M4 | propene-maleic acid[1] | 20.3% | 120 | isopropanol/acetone: 30:1 |
| M5 | ethene-acrylic acid (4:1)[2] | 20.0% | 140 | THF/acetone 3:1 |
| M6 | vinyl ether maleic anhydride[2] | 45.0% | 150 | DMF |
| M7 | ethene-maleic anhydride[2] | 53.0% | 260 | n-propanol/MEK; 10:1 |
| M8 | styrene-acrylic acid (4:1)[1] | 19.0% | 130 | isopropanol/acetone 30:1 |
| M9 | ethene-maleic acid reacted with hepta-decylsuccinimide | 21% | 190 | dioxane |
| M10 | 60-octadecene-maleic anhydride | 17.0% | 220 | isopropanol |
| M11 | α-dodecene-maleic anhydride | 15.0% | 170 | isopropanol/acetone 20:1 |
| M12 | C₂₀-α-olefin-maleic anhydride | 21% | 190 | ethanol |

[1]from DE 40 34 901
[2]from DE-A 22 42 818

The Vinyl Monomers Used

For each of the monomers listed in Table 3, (a) 5% strength by weight aqueous solutions, (b) 5% strength by weight isopropanol solutions or (c) 5% strength by weight acetone/THF/water (4:4:1) solutions were prepared.

TABLE 3

Vinyl monomers used including crosslinkers

| Solution Designation | Vinyl monomer |
|---|---|
| V1 | sodium styrenesulfonate |
| V2 | acrylic acid |
| V3 | hydroxyethyl methacrylate |
| V4 | hydroxyethyl acrylate |
| V5 | sodium methallyl sulfate |
| V6 | maleic acid |
| V7 | sodium vinylsulfonate |
| V8 | sugar derivative I[1] |
| V9 | sugar derivative II[2] |
| V10 | acrylonitrile |
| V11 | acrylamide |
| V12 | pentaerythritol triallyl ether |
| V13 | pentaerythritol tetraacrylate |
| V14 | polyethylene glycol (1000) dimethylacrylate |
| V15 | diethylene glycol methacrylate |

TABLE 3-continued

Vinyl monomers used including crosslinkers

| Solution Designation | Vinyl monomer |
|---|---|
| V16 | sodium 4-vinylbenzoate |
| V17 | ethylene glycol dimethacrylate |

[1]O-sulfated 1-hydroxy-1-deoxy-1-(4-vinylphenyl)-D-gluco(D-manno) pentitol as the sodium salt (in accordance with German Patent Application 197 20 369.8 (O.Z. 5195))
[2]- and O-sulfated 1-amino-1-deoxy-1-(4-vinylphenyl)-D-gluco(D-manno) pentitol as the sodium salt (in accordance with German Patent Application 197 20 369.8 (O.Z. 5195))
[3]also crosslinker

Coating Processes

After fixing the macroinitiator and if desired a crosslinker by immersion in its i.e., their solution and drying in air or in a drying cabinet at 50° C., the vinyl monomers and if desired together with a crosslinker are applied to the macroinitiator coat in the manner indicated in Table 6 and cured.

TABLE 4

Coating methods for vinyl monomers

| Coating code | Coating technique |
|---|---|
| BV1 | dipping |
| BV2 | spraying |
| BV3 | brushing |
| BV4 | fixing in the immersed state |

Determination of the Antibacterial Properties

The test for adhesion of bacteria can be carried out with various strains. Particularly suitable for this purpose are the bacteria listed in Table 5, since they occur frequently in clinical isolates from infected catheters.

TABLE 5

Bacterial strains for measuring the primary adhesion

| | Strain |
|---|---|
| B1 | *Staphylococcus aureus* |
| B2 | *Staphylococcus epidermidis* |
| B3 | *Escherichia coli* |
| B4 | *Klebsiella pneumoniae* |

The method of determining the primary adhesion (i.e., independently of subsequent multiplication) of these bacterial strains is described below by way of example for *Klebsiella pneumoniae*. The primary adhesion of the other strains (B1 to B3) was determined analogously.

Determination of the Primary Bacterial Adhesion Under Static Conditions

An overnight culture of the bacterial strain *Klebsiella pneumoniae* in yeast extract-peptone-glucose nutrient medium (1%+1%+1%) is centrifuged and the extract is taken up again in phosphate-buffered saline (=PBS; 0.05 m $KH_2PO$, pH 7.2+0.9% NaCl). The suspension is diluted with PBS buffer to a cell concentration of $10^8$ cells/ml. The suspension bacteria are brought into contact for 3 h with the section of film that is to be investigated. This is done by spiking circular film sections having a diameter of 1.6 cm (=4.02 cm²), coated on both sides, onto a preparation needle and shaking them with the cell suspension. Films coated on one side, in the form of a flat circular disk with a diameter of 4.5 cm and with a supporting membrane of 2–3 cm thick flexible PVC, are clamped into a membrane filter apparatus.

The cell suspension is applied to the upward-facing side bearing the test coating, and is shaken for 3 h. The membrane filter apparatus must be tightly sealed; in other words, no cell suspension must flow out through leakage sites.

After the contact time has elapsed the bacterial suspension is drawn off under suction using a water jet pump and the film sections are washed for 2 minutes by shaking them in a 100 ml glass beaker with 20 ml of sterile PBS solution. The film section is immersed again in sterile PBS solution and then extracted in a boiling water for 2 minutes with 10 ml of heated—TRIS/EDTA (0.1 M trishydroxyethylaminomethane, 4 mM ethylenediaminetetraacetic acid, adjusted to pH 7.8 with HCl).

The extraction solution is used to fill small Eppendorf cups and is immediately frozen at −20° C. until the extracted adhenosine triphosphate (ATP) is determined by bioluminescence. The determination is carried out as follows: 100 µl of reagent mix (bioluminescence test CLS II, BBOEHRINGER MANNHEIN GmbH) are placed in a transparent polycarbonate tube, and the light pulses are integrated over a period of 10 seconds in a light pulse meter LUMAT LB9501 (Laboratorien Prof. Berthold GmbH, 75323 Bad Wildbad, Germany). Then a 100 µl sample is added and measurement is repeated. The relative light units (RLU) are obtained by subtracting the light pulses in the reagent mix from the number of light pulses measured in the complete batch. This value is related to the number of bacteria which have adhered to the film. The conversion factor between the RLU value in the bacterial count is determined by extracting an aliquot of 0.1 ml of the bacterial suspension containing $10^8$ cells/ml in 10 ml of hot TRIS/EDTA and then determining the ATP content.

Results

Table 6 below sets out the various conditions and the results of a total of 12 experiments. The reported values for reduction in bacterial adhesion are always in comparison with the uncoated samples.

TABLE 6

COATING EXPERIMENTS

| Experiment | Substrate | Macroinitiator and if desired crosslinker ratio, concentration | Monomer (ratio) | Monomer solution | Method | Curing | Temperature | Duration | Reduction in bacterial adhesion[1] |
|---|---|---|---|---|---|---|---|---|---|
| 1 | F1 | M10 (2%) | V1 + V2 (35:65) | a | BV4 | therm. | 90° C. | 1 h | 90 |
| 2 | F2 | M8 (5%) | V1 | a | BV4 | therm. | 80° C. | 3 h | 93 |
| 3 | F2 | M2 (3%) | V3 + V7 (1:1) | c | BV3 | UV | 25° C. | 10 min. | 85 |
| 4 | F3 | M1 (1%) | V5 + V6 (:3) | a | BV4 | therm. | 85° C. | 2 h | 89 |
| 5 | F4 | M6 (5%) | V8 + V16 (1:2) | c | BV2 | UV | 25° C. | 5 min. | 94 |
| 6 | F5 | M3 (3%) | V10 | b | BV1 | UV | 25° C. | 4 min. | 90 |
| 7 | F6 | M4 (5%) | V2 + V15 (10:1) | c | BV2 | therm. | 100° C. | 20 min. | 85 |
| 8 | F7 | M12 (3%) | V11 | c | BV1 | UV | 25° C. | 5 min. | 92 |
| 9 | F8 | M5 (1%) | V11 | c | BV2 | therm. | 70° | 3 h | 90 |
| 10 | F9 | M11 (5%) | V2 + V13 (10:1) | b | BV3 | therm. | 80° C. | 30 min. | 85 |
| 11 | F10 | M9 (5%) | V9 + V14 (20:1) | a | BV4 | UV | 25° C. | 5 min. | 94 |
| 12 | F4 | M7 (5%) | V4 + V12 (15:1) | b | BV3 | therm. | 55° C. | 4 h | 80 |
| 13 | F1 | M10 V17 (2:1), (2%) | V2 | a | BV4 | therm. | 90° C. | 3 h | 80 |
| 14 | F1 | M10 V12 (1:1), (2%) | V2 | a | BV4 | therm. | 90° C. | 3 h | 85 |
| 15 | F1 | M10 V12 (1:3), (2%) | V2 | a | BV4 | therm. | 90° C. | 3 h | 90 |
| 16 | Hose 2 | M10 V12 (1:1), (10%) | V2 | a | BV4 | therm. | 90° C. | 3 h | 92 |
| 17 | Hose 1 | M10 V12 (1:1), (10%) | V2 | a | BV4 | therm. | 90° C. | 3 h | 75 |
| 18 | Hose 3 | M10 V12 (1:1), (52) | V2 | a | BV4 | therm. | 90° C. | 3 h | 85 |
| 19 | Hose 4 | M10 V12 (1:1), (5%) | V2 | a (30% monomer) | BV4 | therm. | 90° C. | 30 min. | 90 |
| 20 | Hose 5 | M10 V12 (1:), (5%) | V2 | a (30% monomer) | BV4 | therm. | 90° C. | 30 min. | 92 |

[1]Always in comparison with the uncoated sample.

Determination of the Antithrombic Activity of the Polyamide 12 Film Coated in Experiment 5

The blood coagulation time measured by the partial thromboplastin time (PTT) is affected by anticoagulants such as heparin. To determine the PTT<a contact activator, phospholipids and calcium ions are all added to blood plasma in order to activate the contact activators, and to activate the intrinsic coagulation system. In the practical implementation of the test, the contact activator (e.g., kaolin) and phospholipids (e.g., cephalin) are added to blood plasma and the treated plasma is incubated at 37° C. for 3 minutes in the presence of the coated PA 12 film and, for comparison, in the presence of an uncoated PA 12 film. Then calcium chloride is added and the coagulation time (PTT) is measured.

The PTT time for the uncoated PA 12 film is 35 seconds, that for the film coated in accordance with Experiment 5 60 seconds. The values are means from measurements with blood plasmas from three donors.

The thrombin time (TT) is a further measure of the anticoagulant action of a substance. In the final phase of coagulation fibrinogen turns into the insoluble fibrin, a soft coagulum, which is transformed by covalent cross-linking into hard coagulum (clot). This reaction is catalyzed by thrombin and retarded by anticoagulants such as heparin. To determine the heparin-analogous activity, the TT of the coated PA 12 film was compared with the TT of the uncoated PA 12 film.

The TT of the uncoated PA 12 film was 21 seconds, that of the PA 12 film coated in accordance with Experiment 5 26 seconds.

Having described the present invention it will now be apparent to the artisan that many changes and modifications may be made to the above-described embodiments without departing from the spirit and the scope of the present invention.

What is claimed as new and is desired to be secured by Letters Patent of the United States is:

1. A process for coating a surface of a substrate, comprising:
   treating the surface of said substrate with a macroinitiator having a free-radical forming group in a side chain;
   graft polymerizing at least one vinyl monomer of formula (I):

$$R\text{---}(A)_{a1} \tag{I}$$

on the surface of said substrate by treating said monomer with radiation or heat, thereby providing a coated surface;
   wherein in formula (I)
   R is an olefinically unsaturated organic radical having a valence a;
   A is a carboxyl group, sulfuric acid group, sulfonic acid group, phosphonic acid group, phosphoric acid group, phosphorous acid group, phenolic hydroxyl group, a salt of a carboxyl group, a salt of a sulfuric acid group, a salt of a sulfonic acid group, a salt of a phosphonic acid group, a salt of a phosphoric acid group, a salt of a phosphorous acid group or a salt of a phenolic hydroxyl group; and
   a is an integer of from 1 up to and including 6; and
   if A is said carboxyl group or said salt of the carboxyl group, then said vinyl monomer contains either at least one further radical A having definitions specified for A or said vinyl monomer is used together with at least one further monomer I in which A has a different one of the definitions specified for A.

2. The process of claim 1, wherein said vinyl monomer of formula (I) is represented by a vinyl monomer of formula (II):

$$(C_nH_{2n-9-x})(COOR^1)_x \tag{II}$$

or by a vinyl monomer of formula (III)

$$(C_nH_{2n-9-x})(SO_3R^1)_x \tag{III}$$

wherein
   n independently at each occurrence is an integer from 2 up to and including 6;
   x independently at each occurrence is 1 or 2;
   q independently at each occurrence is 0 or, if n=4, 5 or 6, then q is 2; and
   $R^1$ independently at each occurrence is hydrogen or one equivalent of a metal ion.

3. The process of claim 1, wherein said vinyl monomer of formula (I) is represented by a vinyl monomer of formula (IV):

$$(C_6H_{6-b-c-d})B_bR^3{}_c(OH)_d \tag{IV}$$

wherein
   B independently at each occurrence is a mono- or divalent straight chain or branched radical of the formula $(C_nH_{2n-1-q-y})(COOR^1)_y$ or $(C_nH_{2n-1-q-x})(SO_3R^1)_y$, where n independently at each occurrence is an integer from 2 up to and including 6; q independently at each occurrence is 0 or, if n=4, 5 or 6, then q is 2; $R^1$ independently at each occurrence is hydrogen or one equivalent of a metal ion; and y is 0, 1 or 2;
   $R^3$ independently at each occurrence is $C_{1-4}$-alkyl, —$NH_2$, —COOH, —$SO_3H$, —$OSO_3H$, —$OPO(OH)_2$, —$PO(OH)_2$—$OPO(O^-)OCH_2$—$CH_2$—$N^+(CH_3)_3$, —$PO(O^-)O$—$CH_2$—$CH_2$—$N^+(CH_3)_3$, —$OP(O^-)PCH_2$—$CH_3$—$N^+(CH_3)_3$;
   b is an integer of from 1 to 3;
   c is an integer of from 0 to 3; and
   d is an integer of from 0 to 3;
with the proviso that b+c+d≦6.

4. The process as in any one of claims 1–3, wherein the vinyl monomers (I), (II), (III) and (IV) are chosen such that the grafted coatings contain carboxyl groups or carboxylate groups or both and sulfonic groups or sulfonate groups or both.

5. The process of claim 3, wherein the molar ratio of carboxyl groups or carboxylate groups or both to sulfonic acid or sulfonate groups or both is from about 0.2 to 3.

6. The process of claim 3, wherein the molar ratio of carboxyl groups or carboxylate groups or both to sulfonic acid or sulfonate groups or both is from about 0.4 to 3.

7. The process of claim 3, wherein the molar ratio of carboxyl groups or carboxylate groups or both to sulfonic acid or sulfonate groups or both is from about 0.4 to 2.

8. The process of claim 3, wherein the molar ratio of carboxyl groups or carboxylate groups or both to sulfonic acid or sulfonate groups or both is from about 2 to 10.

9. The process of claim 3, wherein the molar ratio of carboxyl groups or carboxylate groups or both to sulfonic acid or sulfonate groups or both is from about 3 to 10.

10. The process of claim 3, wherein the molar ratio of carboxyl groups or carboxylate groups or both to sulfonic acid or sulfonate groups or both is from about 3 to 5.

11. The process of claim 1, wherein the graft polymerization of the vinyl monomers is brought about by rays in the range from about 250 to 500 nm.

12. The process of claim 1, wherein said radiation is UV-radiation in the range of from about 290 to 320 nm.

13. The process of claim 1, wherein the polymerization is initiated by heat.

14. The process of claim 13, wherein a temperature is from about 30 to 120° C.

15. The process of claim 1, further comprising reducing adhesion and propagating bacteria on said coated surface.

16. The process of claim 5, wherein said bacteria are selected from the group consisting of *Staphylococcus aureus, Staphylococcus epidermis, Streptococcus pyogenes, Klebsiella neumoniae, Pseudomonas aeruginosa* and *Escherichia coli*.

17. The process of claim 1, wherein said coated surface has cell proliferation inhibiting properties.

18. The process of claim 1, wherein said coated surface has cell proliferation promoting properties.

19. The process of claim 1, wherein said substrate comprises a plastic, a naturally occurring rubber, a synthetic-rubber, a metal, wood or glass.

20. The process of claim 1, wherein said substrate is a polymer substrate in the form of sheets, films, tubes or hoses.

21. The process of claim 1, wherein, in addition to said vinyl monomer of formula (I), a crosslinking vinyl monomer which has at least 2 olefinic double bonds is polymerized.

22. The process of claim 1, wherein, in addition to said vinyl monomer of formula (I), a crosslinking vinyl monomer which has 3 or 4 olefinic double bonds is polymerized.

23. The process of claim 1, wherein a crosslinking vinyl monomer is used together with the macroinitiator in the treatment of substrate.

24. The process of claim 1, wherein a crosslinking monomer, optionally together with said vinyl monomer of formula (I) wherein R is a monoolefinically unsaturated organic radical, is applied to the substrate treated with said macroinitiator.

25. The process of claim 1, wherein the vinyl monomer is chosen such that the grafted polymer layer comprises phosphoric acid groups or phosphoric acid groups or salts or esters thereof.

\* \* \* \* \*